United States Patent
Gleich (10) Patent No.: US 8,154,276 B2
(45) Date of Patent: Apr. 10, 2012

(54) METHOD AND ARRANGEMENT FOR LOCATING MAGNETIC MARKERS IN A REGION OF ACTION

(75) Inventor: Bernhard Gleich, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 486 days.

(21) Appl. No.: 12/519,780

(22) PCT Filed: Dec. 17, 2007

(86) PCT No.: PCT/IB2007/055162
§ 371 (c)(1),
(2), (4) Date: Jun. 18, 2009

(87) PCT Pub. No.: WO2008/078266
PCT Pub. Date: Jul. 3, 2008

(65) Prior Publication Data
US 2010/0072991 A1     Mar. 25, 2010

(30) Foreign Application Priority Data
Dec. 20, 2006    (EP) .................................... 06126570

(51) Int. Cl.
*G01N 27/72*    (2006.01)
(52) U.S. Cl. ........................................................ 324/228
(58) Field of Classification Search ............... 324/228
See application file for complete search history.

(56) References Cited

U.S. PATENT DOCUMENTS
6,168,780 B1    1/2001    Andra
2003/0085703 A1    5/2003    Gleich FOREIGN PATENT DOCUMENTS
DE    10151778    5/2003
EP    1304542    4/2003
WO    W02006067664    6/2006

OTHER PUBLICATIONS

Gleich, B., et al., "Magnetic Particle Imaging (MPI)", MEDICAMUNDI, vol. 50, No. 1, May 1, 2006, pp. 66-71.
Weitschies, W., et al., "Magnetic Marker Monitoring: An Application of Biomagnetic Measurement Instrumentation and Principles for the Determination of the Gastrointestinal Behavior of Magnetically Marked Solid Dosage Forms", Advanced Drug Delivery Reviews, vol. 57, (2005), pp. 1210-1222.

*Primary Examiner* — Bot Ledynh (57) ABSTRACT

A method and an arrangement for influencing and/or detecting and/or locating magnetic markers in a region of action is disclosed, which method comprises the steps of: generating a magnetic drive field so that the magnetization of the magnetic marker changes, generating a magnetic selection field having a pattern in space of its magnetic field strength providing a magnetic field gradient in the region of action, acquiring a first signal by means of a first receiving probe and acquiring a second signal by means of a second receiving probe, the first receiving probe and the second receiving probe being located at different locations relative to the region of action, the first signal and the second signal depending on the magnetization of the magnetic marker in the drive field and in the selection field and further depending on the location of the magnetic marker, the magnetic selection field having a first magnetic field strength configuration, repeating at least once the acquisition of the first signal and of the second signal in the presence of the selection field having a second magnetic field strength configuration, computing an estimation of the location of the magnetic marker by means of the acquired signals.

18 Claims, 3 Drawing Sheets

METHOD AND ARRANGEMENT FOR LOCATING MAGNETIC MARKERS IN A REGION OF ACTION

CROSS REFERENCE TO RELATED APPLICATIONS

This application claims the benefit of EP provisional application s/n 06126570.8, filed Dec. 20, 2006, which is incorporated herein by reference. Related applications are PCT s/n IB2007/055126, "Arrangement and Method for Influencing and/or Detecting Magnetic Particles in a Region of Action," filed Dec. 14, 2007, PCT s/n IB2007/055152, "Arrangement for Influencing and/or Detecting Magnetic Particles in a Region of Action and Method of Producing a Disk Shaped Coil," filed Dec. 17, 2007, PCT s/n IB2007/055157, "Arrangement and Method for Influencing and/or Detecting Magnetic Particles in a Region of Action," filed Dec. 17, 2007, "Arrangement and Method for Influencing and/or Detecting Magnetic Particles in a Region of Action," filed Dec. 14, 2007, PCT s/n IB2007/055174, "Arrangement and Method for Influencing and/or Detecting Magnetic Particles in a Region of Action," filed Dec. 17, 2007, "Arrangement and Method for Influencing and/or Detecting Magnetic Particles in a Region of Action," filed Dec. 14, 2007, PCT s/n IB2007/055158, "Arrangement and Method for Influencing and/or Detecting and/or Locating Magnetic Particles in a Region of Action," filed Dec. 17, 2007, PCT s/n IB2007/055178, "Arrangement and Method for Detecting and/or Locating a Magnetic Material in a Region of Action, Use of a Arrangement In the Examination of Buildings," filed Dec. 17, 2007, PCT s/n IB2007/055177, "Method and Arrangement for Influencing and/or Detecting Magnetic Particles in a Region of Action," filed Dec. 17, 2007, "Method and Arrangement for Separating Magnetic Particles, Magnetic Particles and Use of Magnetic Particles," filed Dec. 18, 2007, PCT s/n IB2007/055165, "Arrangement and Method for Influencing and/or Detecting Magnetic Particles in a Region of Action, Coil Arrangement," filed Dec. 17, 2007, and PCT s/n IB2007/055163, "Influencing and/or Detecting Magnetic Particles in a Region of Action of a Examination Object," filed Dec. 17, 2007.

The present invention relates to a method for locating magnetic markers and to the use of magnetic markers. Furthermore, the invention relates to an arrangement for locating magnetic markers in a region of action.

A method of such a kind is known from International patent application WO 2006/067664 A2. In the case of the method described in that publication, after the introduction of the marker into the examination region, a magnetic field with a spatial profile of the magnetic field strength is generated such as to produce a first sub-zone with a low magnetic field strength and a second sub-zone with a higher magnetic field strength in the examination region. Thereafter, the spatial position of the two sub-zones in the examination region is varied and signals are recorded and evaluated which depend on the way in which the marker is affected by the variation of the spatial position of the two sub-zones in the examination region.

This has the drawback that the location of the magnetic marker is only determinable with a relatively low spatial resolution.

It is therefore an object of the present invention to provide a method in which the drawbacks of the prior art are avoided or at least reduced.

The above object is achieved by a method for locating at least one magnetic marker in a region of action, wherein the method comprises the steps of generating a magnetic drive field so that the magnetization of the magnetic marker changes, furthermore generating a magnetic selection field having a pattern in space of its magnetic field strength, furthermore acquiring a first signal by means of a first receiving probe and acquiring a second signal by means of a second receiving probe, the first receiving probe and the second receiving probe being located at different locations relative to the region of action, the first signal and the second signal depending on the magnetization of the magnetic marker in the drive field and in the selection field and further depending on the location of the magnetic marker, the magnetic selection field having a first magnetic field strength configuration, furthermore repeating at least once the acquisition of the first signal and of the second signal in the presence of the selection field having a second magnetic field strength configuration, and furthermore computing an estimation of the location of the magnetic marker by means of the acquired signals.

The advantage of such a method is that it is possible to locate the at least one magnetic marker with much higher resolution than according to the prior art. According to the present invention, the influence of the presence of objects that distort the magnetic field can be reduced and therefore the power of spatial resolution can be enhanced because the negative effects of a magnetic field distortion can be largely reduced leading to a comparably higher resolution of the location of the at least one marker. Thereby, it is very beneficial to be able to have a first estimation of the location of the at least one magnetic marker by means of using signals from different receiving probes located at different locations relative to the region of action. This is due to the fact that a magnetic marker located nearer to the first receiving probe than to the second receiving probe will normally (i.e. with identical conditions in other respects) induce a stronger magnetization response in the first signal (the signal provided by the first receiving probe) than in the second signal (the signal provided by the second receiving probe). The first and second receiving probe together are hereinafter also called the receiving means. For the different embodiment of the at least one magnetic marker, reference is made to International Patent Application WO 2006/067664 A2 which is hereby incorporated by reference in its entirety.

According to a preferred embodiment of the present invention, the acquisition of the first signal and of the second signal in the presence of the selection field is repeated several times with different magnetic field strength configurations of the selection field and/or the first signal and the second signal are acquired simultaneously. Preferably, the selection field provides a magnetic field gradient in the region of action. Thereby, it is very advantageously possible to be able to gather more information about the spatial relationship of the magnetic marker or the plurality of magnetic markers.

Furthermore, it is preferred according to the present invention that the selection field is generated such that a first sub-zone having a low magnetic field strength and a second sub-zone having a higher magnetic field strength are formed in the region of action. Thereby, it is advantageously possible according to the present invention to further vary the magnetic field strength configuration of the selection field.

In a further embodiment of the present invention, it is furthermore preferred that at least a first magnetic marker and a second magnetic marker is present in the region of action and/or the computation of an estimation of the locations of the magnetic markers by means of the acquired signals comprises the step of de-convoluting the acquired signals with a first magnetization response of the first magnetic marker and/or with a second magnetization response of the second magnetic marker. According to still a further embodiment of the present invention, the first magnetization response and the second magnetization response differ respectively depending on the magnetic field strength configuration of the magnetic selection field. Thereby, it is possible to use the inventive method in a very flexible manner.

The invention further relates to an arrangement for locating magnetic markers in a region of action, which arrangement comprises: drive means for generating a magnetic drive field so that the magnetization of the magnetic markers changes, furthermore selection means for generating a magnetic selection field having a pattern in space of its magnetic field strength providing a magnetic field gradient in the region of action, furthermore receiving means for acquiring signals, the receiving means comprising a first receiving probe and a second receiving probe, a first signal being acquired by means of the first receiving probe and a second signal being acquired by means of the second receiving probe, the first receiving probe and the second receiving probe being located at different locations relative to the region of action, the first signal and the second signal depending on the magnetization of the magnetic markers in the drive field and in the magnetic selection field and further depending on the locations of the magnetic markers, and furthermore computation means for computing an estimation of the locations of the magnetic markers by means of the acquired signals while the magnetic selection field having at least a first magnetic field strength configuration and a second magnetic field strength respectively.

With the inventive arrangement, it is advantageously possible to reduce the negative effects of the distortion of magnetic fields due to the presence of magnetic markers.

According to a preferred embodiment of both the method and of the arrangement of the present invention, the first magnetic field strength configuration or the second magnetic field strength configuration of the selection field corresponds to a switched off selection field and/or the magnetic field strength configuration of the magnetic selection field is continuously changed between successive acquisitions of the first signal and the second signal. Thereby, it is possible to acquire information at different magnetic field strength configurations of the magnetic selection field in a relatively simple manner.

According to a further preferred embodiment of both the method and of the arrangement of the present invention, the magnetic markers comprise at least partially a non-ferromagnetic material or a paramagnetic material. Thereby, it is advantageously possible to use magnetic markers of quite different nature and suitable for the intended use.

The invention further relates to a computer program for an inventive arrangement for carrying out the inventive method and to a computer program product comprising such a computer program.

The present invention further refers to the use of at least one magnetic marker in the inventive arrangement or with the method according to the present invention.

According to the present invention, it is to be understood that the selection means and/or the drive means and/or the receiving means can at least partially be provided in the form of one single coil or solenoid. However, it is preferred according to the present invention that separate coils are provided to form the selection means, the drive means and the receiving means. Furthermore according to the present invention, the selection means and/or the drive means and/or the receiving means can each be composed of separate individual parts, especially separate individual coils or solenoids, provided and/or arranged such that the separate parts form together the selection means and/or the drive means and/or the receiving means. Especially for the drive means and/or the selection means, a plurality of parts, especially pairs for coils (e.g. in a Helmholtz or Anti-Helmholtz configuration) are preferred in order to provide the possibility to generate and/or to detect components of magnetic fields directed in different spacial directions.

According to the present invention, it is preferred that the selection means and/or the drive means and/or the receiving probes comprises at least partially a litz wire/stranded wire and preferably that the litz wire comprises a plurality of individual wires, each individual wire being surrounded by an electrically high resistive material. It is thereby possible to provide a very high current supporting surface inside the drive means and/or the receiving means which is important both for the case that an AC current with a comparably high frequency is to be supported and for the case that a DC current or an AC current having a comparably low frequency is to be supported by the drive means and/or the receiving means but in the presence of a static and/or an dynamic magnetic field that penetrates the drive means and/or the receiving means. In still a further preferred embodiment of the present invention, the current supporting paths (e.g. the individual wires of the litz wire) are arranged such that the resistance in a given working frequency band and in a given electromagnetic field penetrating the current supporting paths is substantially minimal, i.e. dominated by thermal noise, especially generated by thermal noise in the region of action. This is achieved in particular by means of carefully defining the individual current paths (e.g. individual wires), current strength, coil configuration and other characteristics of the current supporting paths of the selection means and/or of the drive means. Furthermore and in the case of current supporting paths in the form of litz wires, it is preferred that the litz wire has a ratio of the summed cross sectional area of the individual wires relative to the cross sectional area of the litz wire (filling factor) in a specified range and/or that the individual wires of the litz wire have a diameter of approximately 1 µm to approximately 50 µm, preferably of approximately 10 µm to approximately 25 µm. It is thereby possible to greatly enhance the used current supporting surface inside the litz wire and therefore to realise a reduced resistance of the overall configuration of the selection means and/or of the drive means and/or of the receiving means. Typically, the filling factor of the litz wire of the selection means and/or of the drive means is in the range of about 0.30 to about 0.70, preferably in the range of around 0.50, and therefore higher than the filling factor of the litz wire of the receiving means which is in the range of about 0.01 to about 0.20, preferably in the range of about 0.03 to about 0.10. Furthermore, the diameter of the individual wires of the litz wire of the selection means and of the drive means can be chosen higher than the diameter of the individual wires of the litz wire of the receiving means. According to the present invention, it is very advantageous to take into consideration a change in conducting properties of selection means or drive means if these means are penetrated by the magnetic field of each other. The resistance of the selection means, the drive means and/or the receiving means should be chosen as low as possible in the given environment or penetration pattern. The selection means and the drive means together are also called "field generator means". The selection means comprise magnetic field generation means that provide either a static (gradient) magnetic selection field and/or a comparably slowly changing long range magnetic selection field with frequencies in the range of about 1 Hz to about 100 Hz. Both the static part and the comparably slowly changing part of the magnetic selection field can be generated by means of a permanent magnet or by means of coils or by a combination thereof. The drive means comprise magnetic field generation means that provide a magnetic drive field with frequencies in the range of about 1 kHz to about 200 kHz, preferably about 10 kHz to about 100 kHz. At least part of the field generator means (i.e. the selection means and the drive means) can be implemented by discrete coils where the diameter of the current supporting path (or the individual wires in the case of litz wire) of each coil or of each field generator means has to be chosen in such a way that the skin effect does not increase the resistance of the coil.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described of illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

Figure 1:
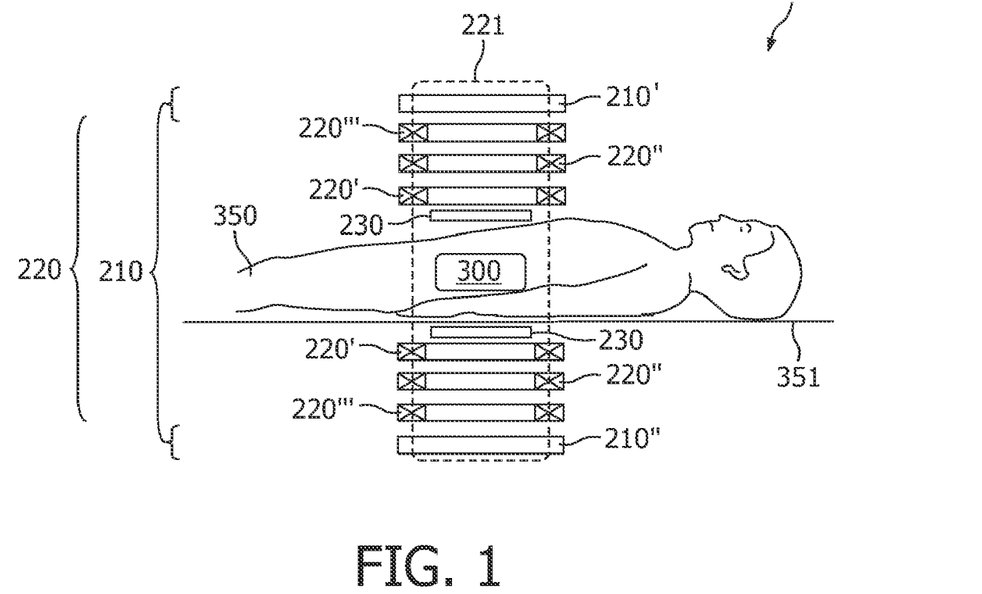
FIG. 1 illustrates schematically an arrangement according to the present invention for carrying out the method according to the present invention.

In FIG. 1, an arbitrary object to be examined by means of an arrangement 10 according to the present invention is shown. The reference numeral 350 in FIG. 1 denotes an object, in this case a human or animal patient, who is arranged on a patient table, only part of the top of which is shown. Prior to the application of the method according to the present invention, magnetic markers 100 (not shown in FIG. 1) are arranged in a region of action 300 of the inventive arrangement 10. Especially prior to a therapeutical and/or diagnostical treatment of, for example, a tumor, the magnetic markers 100 are positioned in the region of action 300, e.g. by means of a liquid (not shown) comprising the magnetic markers 100 which is injected into the body of the patient 350.

According to the present invention, a so-called magnetic drive field 221 is generated in the region of action 300 by drive means 220. The magnetic drive field 221 is preferably variable in time, e.g., by means of an AC current in a coil of the drive means 220, for example with a sinusoidal variation. The magnetic markers 100 experience this magnetic drive field 221 inside the region of action 300. The inventive arrangement 10 further comprises selection means 210 that serve to provide a magnetic field strength configuration inside the region of action by means of a magnetic selection field 211.

In order to generate the magnetic drive field 221 for any given direction in space, there are provided three coil pairs, namely a first coil pair 220', a second coil pair 220" and a third coil pair 220''' which together are called drive means 220 in the following. For example, the first coil pair 220' generates a component of the magnetic drive field 221 which extends in a given direction, i.e. for example vertically. To this end the windings of the first coil pair 220' are traversed by equal currents in the same direction. The two coil pairs 220", 220''' are provided in order to generate components of the magnetic drive field 221 which extend in a different direction in space, e.g. horizontally in the longitudinal direction of the region of action 300 (or the patient 350) and in a direction perpendicular thereto. If second and third coil pairs 220", 220''' of the Helmholtz type were used for this purpose, these coil pairs would have to be arranged to the left and the right of the region of treatment or in front of and behind this region, respectively. This would affect the accessibility of the region of action 300 or the region of treatment 300. Therefore, the second and/or third magnetic coil pairs or coils 220", 220''' are also arranged above and below the region of action 300 and, therefore, their winding configuration must be different from that of the first coil pair 220'. Coils of this kind, however, are known from the field of magnetic resonance apparatus with open magnets (open MRI) in which a radio frequency (RF) coil pair is situated above and below the region of treatment, said RF coil pair being capable of generating a horizontal, temporally variable magnetic field. Therefore, the construction of such coils need not be further elaborated herein.

The arrangement 10 according to the present invention further comprise receiving means 230 that are only schematically shown in FIG. 1. The receiving means 230 usually comprise coils that are able to detect the signals induced by magnetization pattern of the magnetic markers 100 in the region of action 300. Coils of this kind, however, are known from the field of magnetic resonance apparatus in which e.g. a radio frequency (RF) coil pair is situated around the region of action 300 in order to have a signal to noise ratio as high as possible. Therefore, the construction of such coils need not be further elaborated herein. According to the present invention, it is preferred that the resistance of the receiving means is dominated by thermal noise, especially generated by thermal noise due to the presence of the magnetic particles in the region of action, i.e. the resistance of the current supporting paths without the presence of the magnetic particles in the region of action is comparable or smaller than the resistance in presence of the magnetic particles in the region of action. This is achieved in particular by means of carefully defining the individual current paths, current strength, wire configuration and other characteristics of the receiving means.

The arrangement 10 further comprises a plurality of coils forming a selection means 210 whose range defines the region of action 300 which is also called the region of treatment 300. For example, the selection means 210 is arranged above and below the patient 350 or above and below the table top. For example, the selection means 210 comprise a first pair of coils 210', 210'', each comprising two identically constructed windings 210' and 210'' which are arranged coaxially above and below the patient 350 and which are traversed by equal currents, especially in opposed directions. The first coil pair 210', 210'' together are called selection means 210 in the following. Preferably, direct currents are used in this case.

Figure 2:
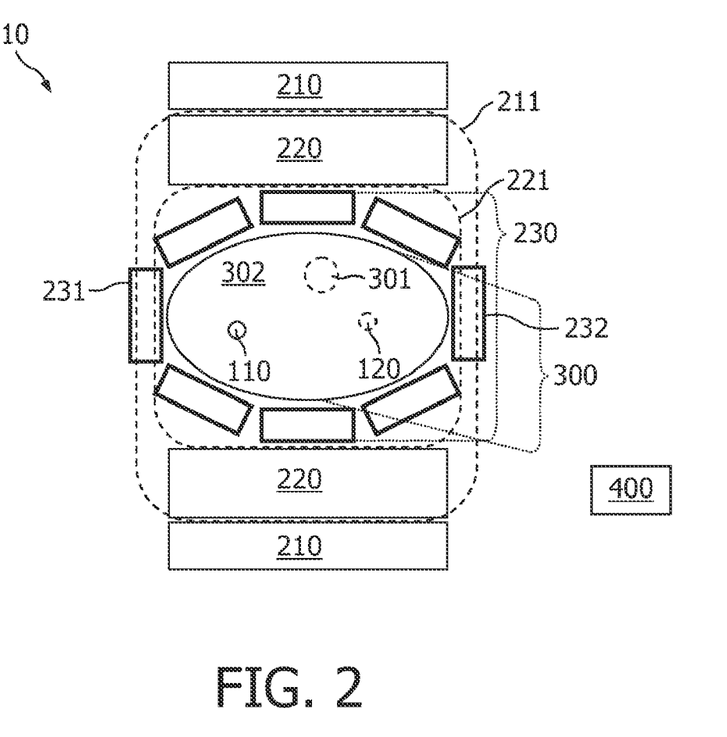
FIG. 2 illustrates schematically a further representation of an arrangement according to the present invention with more details of the region of action and the receiving means.

FIG. 2 schematically represents an arrangement 10 according to the present invention where the selection means 210, the drive means 220 and the receiving means 230 are depicted schematically in relation to a representation of the region of action 300 and two individual magnetic markers, namely a first magnetic marker 110 and a second magnetic marker 120. The drive means 220 generates the magnetic drive field 221. In the example depicted in FIG. 2, the receiving means 230 comprise a first receiving probe 231 and a second receiving probe 232. These two receiving probes 231, 232, which are preferably realized by means of coils or solenoids, e.g. of litz wire, are described as being representatives for preferably a plurality of receiving probes—commonly constituting the receiving means 230—which are not individually referred to by reference signs. Accordingly, the two magnetic markers 110, 120 can also be representatives for a plurality of magnetic markers which are not individually referred to by reference signs. Nevertheless, it is also possible to only use one or two magnetic marker.

The selection means 210 generate a magnetic selection field 211 which is in general a gradient magnetic field. Preferably—but not necessarily—, the selection means 210 define in the region of action 300 a first sub-zone 301 of relatively low magnetic field strength and a second sub-zone 302 of higher magnetic field strength. In this embodiment of the inventive arrangement 10, the first sub-zone 301 comprises a so-called field-free point. The selection means 210 generate the magnetic selection field 211 which is represented in FIG. 2 schematically by a dashed line. It has a substantially constant gradient (e.g. in the direction of the (e.g. vertical) axis of a coil pair of the selection means 210) and reaches the value zero in the field-free point in the first sub-zone 301. Starting from this field-free point (not individually shown in FIG. 2), the field strength of the magnetic selection field 211 (if present) increases in all three spatial directions as the distance increases from the field-free point.

According to the present invention, the magnetic marker 110, 120 is provided such that it is saturated at a comparably low magnetic field. Therefore—if the magnetic selection field 211 is switched on—, more or less all of the magnetic markers inside the second sub-zone 302 (i.e. in the residual part of the region of action 300 outside of the first sub-zone 301 which is denoted by a dashed line around the field-free point) experience a relatively high field strength of the magnetic selection field 211 and therefore behave differently in the presence of the magnetic drive field 221 than without the activation of the magnetic selection field 211. Therefore, also the magnetization response of the magnetic marker 110, 120 is different if it is located in the second sub-zone 302 and if the magnetic selection field 211 is switched on. The field-free point or first sub-zone 301 of the region of action 300 is preferably a spatially coherent area; it may also be a punctiform area or else a line or a flat area. By changing the position of the two sub-zones 301, 302 within the region of action 300, the (overall) magnetization in the region of action 300 changes. By measuring the magnetization in the region of action 300 or by measuring a physical parameters influenced by the magnetization, information about the localization and/or the spatial distribution of the magnetic marker in the region of action can be obtained which is explained in the following.

According to the present invention, the magnetic marker 110, 120 inside the region of action 300 experience the temporally changing magnetic drive field 220 in the presence of the magnetic selection field 211 having a first magnetic field strength configuration. This results in a (changing) magnetization pattern in the region of action 300 which is detected by the receiving probes 231, 232. Due to the temporally changing drive field 220 and the non-linear response of the magnetization of the marker 110, 120, signals are induced in the first and second receiving probes 231, 232 which are attributable to the magnetic marker 110, 120. A first estimate for the location of the marker 110, 120 can be obtained by performing a de-convolution operation similar to the signal treatment in paragraphs 45 to 56 of European Patent Application EP 1304542 A2, which is hereby incorporated by reference in its entirety. For such a de-convolution operation, it is helpful if—for the case of two or more magnetic markers—the magnetic markers 110, 120 are of the same kind, i.e. generating a magnetization response of the same kind if placed at the same location. Nevertheless, also for the case of different magnetic markers 110, 120, it is possible to deduce a first estimate of the position of the magnetic markers 110, 120 by means of an analysis of the first signal 231' and the second signal 232' of the first and second receiving probes 231, 232. The configuration of the selection field 211 such that a first sub-zone 301 and a second sub-zone 302 exists and the variation or the displacement of the first sub-zone 301 in most parts of the region of action 300 further helps to deduce a first estimate of the position of the magnetic markers 110, 120. According to one special embodiment, the magnetic selection field 211 can also be switched off for constituting the first or the second magnetic field strength configuration.

In order to further refine the first estimate of the position of the magnetic marker or markers 110, 120 and in order to be able to provide a relatively high accuracy or resolution in this determination of the location of the magnetic marker or markers, the measurements by the first and second receiving probes 231, 232 are repeated in the presence of a magnetic selection field of a different magnetic field strength configuration (also called second magnetic field strength configuration). For example, the second magnetic field strength configuration corresponds to the first magnetic field strength configuration with the difference, that the magnetic selection field 211 comprises a further component such that a time-constant gradient magnetic field is added to the first magnetic field strength configuration of the magnetic selection field 211. By repeating the measurements in the presence of the magnetic drive field 221 by the first and second receiving probe 231, 232, i.e. by acquiring the first signal 231' and the second signal 232', it is possible to obtain further information about the location of the magnetic marker 110, 120 because the additional time-constant gradient field leads to a changed behaviour of the magnetization (magnetization response) of the marker 110, 120.

In embodiments of the present invention where the first sub-zone 301 (travelling in the region of action 300 by means of the action of the magnetic drive field 221) is present, the additional time-constant gradient field leads to a shift in the time domain of the first signal 231' and of the second signal 232' of the magnetization response of the marker 110, 120

(due to the first sub-zone 301 reaching the magnetic marker 110, 120 earlier or later). This shift can be used according to the present invention to further refine the estimation of the localization of the marker or the markers.

In embodiments of the present invention where the first sub-zone 301 is not present and if the different behaviours of the marker 110, 120 in the presence of different time-constant magnetic gradient fields are known prior to the measurements, further information about the localization of the magnetic marker 110, 120 are accessible.

Generally, by means of a higher number of measurements (repetitions), a more precise information about the distribution and localization of a plurality of magnetic markers 110, 120 or about the localization of a single magnetic marker 110, 120 can be obtained. According to the present invention, the repetition of the measurements in the presence of further different magnetic field strength configurations is possible. Thereby, it is possible according to the present invention that distortion effects in the region of action 300 of objects (e.g. aluminium structures for example an examination table) that could potentially distort especially the magnetic drive field can be reduced by the arrangement and the method according to the present invention. Thereby, magnetic markers can be used as local DC field or AC field magnetic sensors. Due to the fact that a magnetic DC field is not distorted, it is possible to determine the magnetic field (especially the magnetic AC field) at the position of the markers without distortions by applying a sufficient DC field at this position.

The frequency ranges usually used for or in the different components of the selection means 210, drive means 220 and receiving means 230 are roughly as follows: The magnetic field generated by the selection means 210 does either not vary at all over the time or the variation is comparably slow, preferably between approximately 1 Hz and approximately 100 Hz. The magnetic field generated by the drive means 220 varies preferably between approximately 10 kHz and approximately 300 kHz. The magnetic field variations that the receiving means are supposed to be sensitive are preferably in a frequency range of approximately 50 kHz to approximately 10 MHz.

Figure 3:
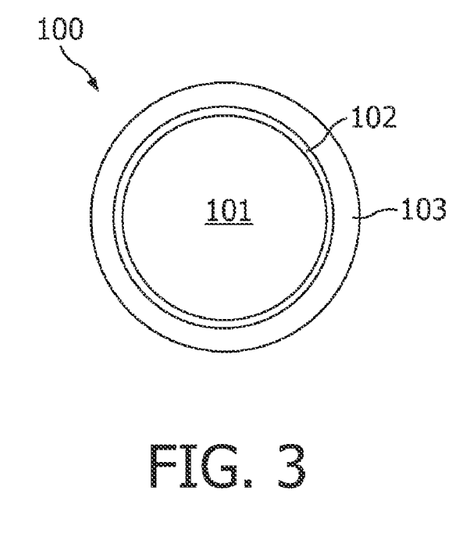
FIG. 3 illustrates schematically an enlarged view of a magnetic particle that can be present in the region of action.

The magnetic marker 100 can be provided by means of objects containing magnetic particles 500. Further examples of magnetic markers 100 are given in WO 2006/067664 A2. Furthermore, such particles 500 can also be provided in the region of action 300 and the arrangement 10 can be used to measure the distribution of these particles. FIG. 3 shows an example of a magnetic particle 500 of the kind which can be used together with an arrangement 10 of the present invention. It comprises for example a spherical substrate 501, for example, of glass which is provided with a soft-magnetic layer 502 which has a thickness of, for example, 5 nm and consists, for example, of an iron-nickel alloy (for example, Permalloy). This layer may be covered, for example, by means of a coating layer 503 which protects the marker 500 against chemically and/or physically aggressive environments, e.g. acids. The magnetic field strength of the magnetic selection field 211 required for changing the behavior of the magnetization of such markers 500 is dependent on various parameters, e.g. the diameter of the markers 500, the used magnetic material for the magnetic layer 502 and other parameters.

For further details of the preferred magnetic particles 100, the corresponding parts of DE 10151778 are hereby incorporated by reference, especially paragraphs 16 to 20 and paragraphs 57 to 61 of EP 1304542 A2 claiming the priority of DE 10151778.

Figure 4:
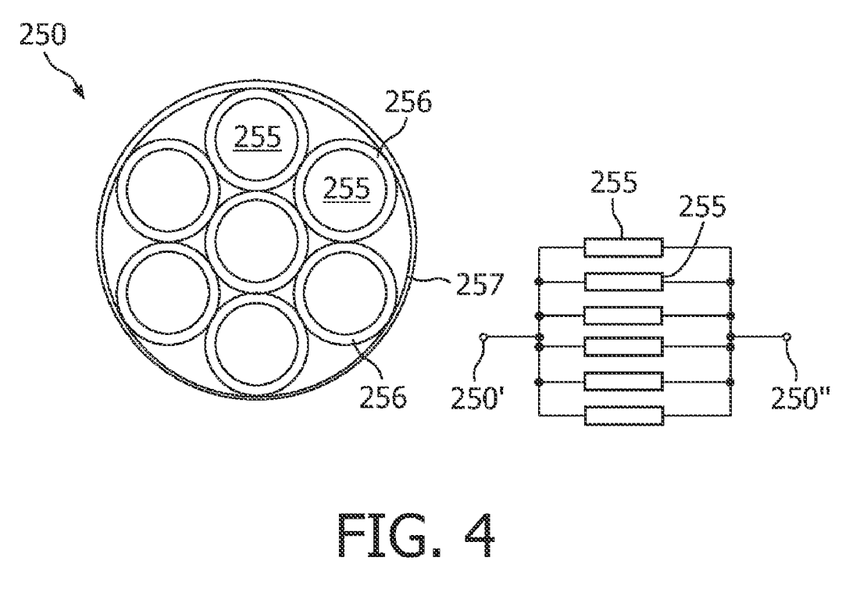
FIGS. 4 to 6 illustrate schematically different examples of litz wire configurations.
Figure 5:
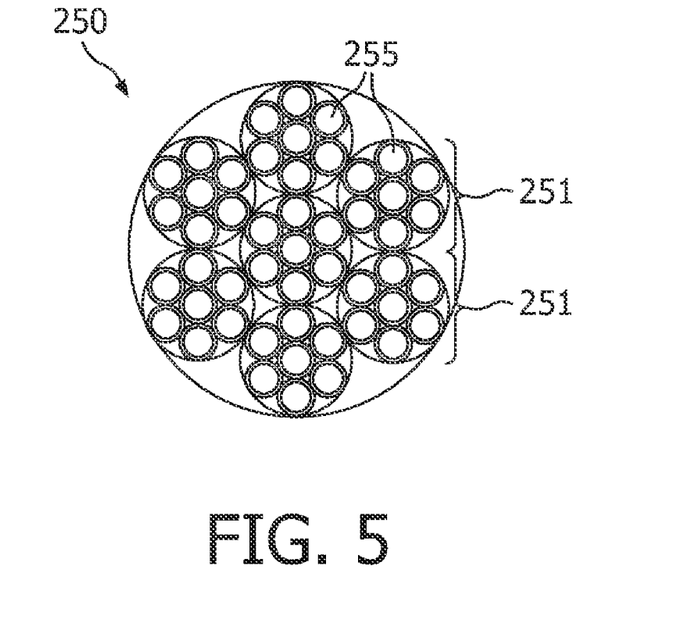
Figure 6:
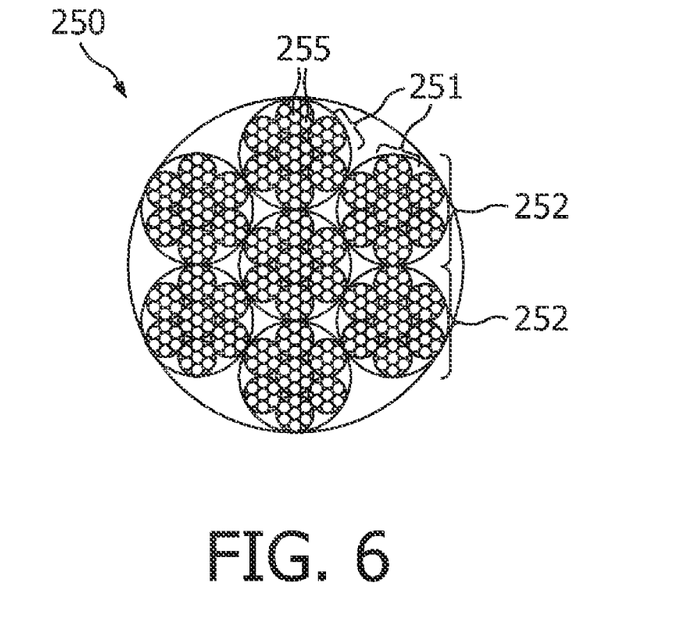

In FIGS. 4 to 6, litz wire 250 is shown in a schematical representation. The litz wire 250 is shown as one example to provide at least one current supporting path inside the selection means 210, the drive means 220 and/or the receiving means 230. Each of the FIGS. 4 to 6 represents a cross sectional view of one embodiment of such a litz wire 250. Each litz wire 250 comprises a multitude of individual wires 255. Thereby, an increase in current supporting surface is possible and the complexity of the handling requirements—especially the possibility of bending the litz wire (in order to form solenoids or coils) comprising a multitude of individual wires—are reduced. The representations of the various embodiments are not drawn to scale and the dimensions are chosen for the sake of representation simplicity only. The filling factor of the litz wire 250 can easily be evaluated by means of summing up the cross sectional areas of each of the individual wires 255 and dividing by the cross sectional area of the complete litz wire 250. By means of applying a pressure to the embodiments of the litz wire 250 represented in FIGS. 4 to 6 in a direction perpendicularly to the longitudinal extension of the litz wire 250, the filling factor can be enhanced. Each individual wire 255 is preferably surrounded circumferentially by an electrically high resistive material 256 which acts in the manner of a cladding 256 for each individual wire 255. It is to be understood that it is preferred according to the present invention that such a cladding material 256 is present at each individual wire 255; however such a continuous cladding 256 is not necessary if the condition is fulfilled that each individual wire 255 of the litz wire 250 is electrically isolated from the adjacent individual wires 250 between a first end 250' of the litz wire and a second end 250" of the litz wire 250. The individual wires 255 of the litz wire 250 act as individual current supporting paths 255 and can be regarded as resistors connected in parallel and having ideally an identical impedance as shown by the equivalent circuit diagram represented on the right hand side in FIG. 4. In the embodiment of the litz wire 250 represented in FIG. 4, a further preferred feature of the litz wire 250 is represented, namely a plastic foil insulation 257 is provided collectively around the individual wires 255. Such a plastic (e.g. thermoplastic) insulation can also be provided to all the other embodiments of the litz wire 250 but is not shown there. The additional feature of such an insulation foil or insulation material 257 collectively around the individual wires 255 of the litz wire 250 provides the advantage that a better high voltage performance of the litz wire is possible.

In FIG. 5 a cross sectional view of a further embodiment of the litz wire 250 is schematically shown where the litz wire 250 comprises also a plurality of individual wires 255 (as in the embodiment according to FIG. 4) but with the individual wires 255 grouped in a plurality of so-called first order litz wires 251. These first order litz wires 251 (each comprising a plurality of individual wires 255) are combined together to form the litz wire 250. In FIG. 5, the continuous cladding 256 is preferably present around each individual wire 255 but not indicated by means of a reference numeral.

In FIG. 6 a cross sectional view of a still further embodiment of the litz wire 250 is schematically shown where the litz wire 250 comprises also a plurality of individual wires 255 (as in the embodiments according to FIGS. 4 and 5) and a plurality of first order litz wires 251 but with the first order litz wires 251 grouped in a plurality of so-called second order litz wires 252. These second order litz wires 252 (each comprising a plurality of first order litz wires 251) are combined together to form the litz wire 250. In FIG. 6, the continuous cladding 256 is preferably present around each individual wire 255 but not represented for the sake of simplicity.

The invention claimed is:

1. A method for locating at least one magnetic marker (100) in a region of action (300), wherein the method comprises the steps of
generating a magnetic drive field (221) so that the magnetization of the magnetic marker (100) changes,
generating a magnetic selection field (211) having a pattern in space of its magnetic field strength,
acquiring a first signal (231') by means of a first receiving probe (231) and acquiring a second signal (232') by means of a second receiving probe (232), the first receiving probe (231) and the second receiving probe (232) being located at different locations relative to the region of action (300), the first signal (231') and the second signal (232') depending on the magnetization of the magnetic marker (100) in the drive field (221) and in the selection field (211) and further depending on the location of the magnetic marker (100), the magnetic selection field (211) having a first magnetic field strength configuration,
repeating at least once the acquisition of the first signal (231') and of the second signal (232') in the presence of the selection field (211) having a second magnetic field strength configuration,
computing an estimation of the location of the magnetic marker (100) by means of the acquired signals (231', 232').

2. A method according to claim 1, wherein the acquisition of the first signal (231') and of the second signal (232') in the presence of the selection field (211) is repeated several times with different magnetic field strength configurations of the selection field (211), the selection field (211) providing preferably a magnetic field gradient in the region of action (300).

3. A method according to claim 1, wherein the first signal (231') and the second signal (232') are acquired simultaneously.

4. A method according to claim 1, wherein the first magnetic field strength configuration or the second magnetic field strength configuration of the selection field (211) corresponds to a switched off selection field (211).

5. A method according to claim 1, wherein the magnetic field strength configuration of the magnetic selection field (211) is continuously changed between successive acquisitions of the first signal (231') and the second signal (232').

6. A method according to claim 1, wherein the selection field (211) is generated such that a first sub-zone (301) having a low magnetic field strength and a second sub-zone (302) having a higher magnetic field strength are formed in the region of action (300).

7. A method according to claim 1, wherein at least a first magnetic marker (110) and a second magnetic marker (120) is present in the region of action (300).

8. A method according to claim 7, wherein the computation of an estimation of the locations of the magnetic markers (100) by means of the acquired signals (231', 232') comprises the step of deconvoluting the acquired signals (231', 232') with a first magnetization response (111) of the first magnetic marker (110) and with a second magnetization response (121) of the second magnetic marker (120).

9. A method according to claim 8, wherein the first magnetization response (111) and the second magnetization response (121) differ respectively depending on the magnetic field strength configuration of the magnetic selection field (211).

10. A method according to claim 1, wherein the magnetic markers (100) comprise at least partially a non-ferromagnetic material or a paramagnetic material.

11. A method according to claim 1, wherein the magnetic markers (100) comprise at least partially a ferromagnetic material and/or a ferrimagnetic material and/or an antiferromagnetic material and/or an antiferrimagnetic material and/or.

12. An arrangement (10) for locating magnetic markers (100) in a region of action (300), which arrangement comprises:
drive means (220) for generating a magnetic drive field (221) so that the magnetization of the magnetic markers (100) changes,
selection means (210) for generating a magnetic selection field (211) having a pattern in space of its magnetic field strength providing a magnetic field gradient in the region of action (300),
receiving means (230) for acquiring signals, the receiving means (230) comprising a first receiving probe (231) and a second receiving probe (232), a first signal (231') being acquired by means of the first receiving probe (231) and a second signal (232') being acquired by means of the second receiving probe (232), the first receiving probe (231) and the second receiving probe (232) being located at different locations relative to the region of action (300), the first signal (231') and the second signal (232') depending on the magnetization of the magnetic markers (100) in the drive field (221) and in the magnetic selection field (211) and further depending on the locations of the magnetic markers (100),
computation means (400) for computing an estimation of the locations of the magnetic markers (100) by means of the acquired signals (231', 232') while the magnetic selection field (211) having at least a first magnetic field strength configuration and a second magnetic field strength respectively.

13. An arrangement (10) according to claim 12, wherein the first magnetic field strength configuration or the second magnetic field strength configuration of the selection field (211) corresponds to a switched off selection field (211).

14. An arrangement (10) according to claim 12, wherein the selection field (211) is generated such that a first sub-zone (301) having a low magnetic field strength and a second sub-zone (302) having a higher magnetic field strength are formed in the region of action (300).

15. An arrangement (10) according to claim 12, wherein the magnetic markers (100) comprise at least partially a non-ferromagnetic material or a paramagnetic material.

16. An arrangement (10) according to claim 12, wherein the magnetic markers (100) comprise at least partially a ferromagnetic material and/or a ferrimagnetic material and/or an antiferromagnetic material and/or an antiferrimagnetic material.

17. A computer program for an arrangement (10) according to claim 12 for carrying out a method for locating at least one magnetic marker (100) in a region of action (300), wherein the method comprises the steps of
generating a magnetic drive field (221) so that the magnetization of the magnetic marker (100) changes,
generating a magnetic selection field (211) having a pattern in space of its magnetic field strength,
acquiring a first signal (231') by means of a first receiving probe (231) and acquiring a second signal (232') by means of a second receiving probe (232), the first receiving probe (231) and the second receiving probe (232) being located at different locations relative to the region of action (300), the first signal (231') and the second signal (232') depending on the magnetization of the magnetic marker (100) in the drive field (221) and in the selection field (211) and further depending on the location of the magnetic marker (100), the magnetic selection field (211) having a first magnetic field strength configuration, repeating at least once the acquisition of the first signal (231') and of the second signal (232') in the presence of the selection field (211) having a second magnetic field strength configuration, computing an estimation of the location of the magnetic marker (100) by means of the acquired signals (231', 232').

18. A Computer program product comprising a computer program according to claim 17.

\* \* \* \* \*